(12) United States Patent
Roeloffs (10) Patent No.: US 9,326,671 B2
(45) Date of Patent: May 3, 2016

(54) ADVANCED SPECULUM

(75) Inventor: Bob Roeloffs, Amsterdam (NL)

(73) Assignee: Bridea Hong Kong Ltd., Hong Kong (HK)

( * ) Notice: Subject to any disclaimer, the term of this patent is extended or adjusted under 35 U.S.C. 154(b) by 218 days.

(21) Appl. No.: 14/124,442

(22) PCT Filed: Apr. 6, 2012

(86) PCT No.: PCT/NL2012/050235
§ 371 (c)(1),
(2), (4) Date: Jan. 24, 2014

(87) PCT Pub. No.: WO2012/138225
PCT Pub. Date: Oct. 11, 2012

(65) Prior Publication Data
US 2014/0171747 A1    Jun. 19, 2014

(30) Foreign Application Priority Data

Apr. 6, 2011  (EP) .................... 11161404

(51) Int. Cl.
*A61B 1/32* (2006.01)
(52) U.S. Cl.
CPC ...................... *A61B 1/32* (2013.01)
(58) Field of Classification Search
CPC ........... A61B 1/32; A61B 17/02; A61B 17/28
USPC ................................ 600/201–246
See application file for complete search history.

(56) References Cited

U.S. PATENT DOCUMENTS

| 2009/0069634 A1 | 3/2009 | Larkin |
| 2009/0177044 A1 | 7/2009 | Cohen et al. |
| 2009/0203968 A1 * | 8/2009 | Winslow .................. A61B 1/32 600/220 |

FOREIGN PATENT DOCUMENTS

| CN | 1269706 A | 10/2000 |
| CN | 101869736 A | 10/2010 |
| CN | 201735047 U | 2/2011 |
| EP | 0190014 * | 1/1986 |
| EP | 0190014 A2 | 1/1986 |
| EP | 0190014 A2 * | 8/1986 ............... A61B 1/31 |
| WO | 99/12466 A1 | 3/1999 |

OTHER PUBLICATIONS

International Search Report for PCT/NL2012/050235, mailed May 23, 2012.
Chinese Office Action for a Counterpart Foreign Application dated Apr. 29, 2015.

* cited by examiner

*Primary Examiner* — Christopher Beccia
(74) *Attorney, Agent, or Firm* — Hoffmann & Baron, LLP

(57) ABSTRACT

It is described a surgical instrument such as a speculum comprising longitudinally extending cups-shaped pivotably mounted blades manufactured from a moldable material, such as plastic or metal. Each blade has an inwardly curved circumferential edge with an edge face which is provided with a parting line resulting from molding the blades. Negative effects such as possible injuries associated with parting lines or steps can be mitigated by inwardly relocating these lines on an edge face of the inwardly curved circumferential edge.

18 Claims, 8 Drawing Sheets

ADVANCED SPECULUM

CROSS-REFERENCE TO RELATED APPLICATIONS

This Application is a National Stage of International Application No. PCT/NL2012/050235 filed Apr. 6, 2012, the contents of which is incorporated by reference herein.

BACKGROUND

A speculum is a commonly-used device for opening or distending an orifice or cavity of a body or incision in a body to permit examination of the interior and/or to enable a procedure among which the taking of a sample or treatment of the inspected area.

The basic function of a speculum is to increase the size or diameter of this, orifice, cavity or incision by increasing the distance between two or more surfaces or parts of surfaces of the speculum. The force required for this handling can be supplied manually such as by the squeezing together of two handles. Said force can be applied direct or relayed through technical solutions for example by means of wires, cables and or rods. Said force can also be supplied or relayed electrically, pneumatically or via other forms of energy transfer.

In the medical field specula are available in a variety of forms and for a variety of functions among which, but not limited to, examination of vagina, rectum, ear, nostril, throat, and/or an incision, cavity or orifice in skin, sub dermal tissue or other tissue. To illustrate the current status of available specula the speculum as used in the gynaecological field will be used only by way of example, knowing that specula are also used in the general medical field. Specula are also generally used for opening a cavity, incision or slit in an inanimate object.

Current specula are most commonly made from deformed sheet metal or injection moulded plastic. The standard gynaecological speculum generally consists of two or more blades, essentially having a cup or beak shape. The generally longitudinally extending blades, or beak parts, are normally pivotally joined at one short side, the proximal end and cupped at the outer not pivotable side, the distal end. The beak parts have a thickness, which influences their rigidity. Therefore the plastic beaks are on average thicker than the metal versions to achieve the required strength and stiffness. The sheet metal of the metal beaks generally has a thickness of approximately 1 to 1.2 millimeter. The beaks of plastic specula generally have a thickness of 2 mm to 2.5 millimeters. Beak widths and lengths vary. In general the beak width is a few centimeters at the distal end and may increase towards the proximal end. In comparison to the beak width the edges are relatively thin.

Patent Application Publication US-2009/0203968 describes a surgical instrument in the form of a reusable speculum having blades each with solid rounded edges extending laterally outwardly. The terminal end of these edges show an increase of material thickness which may provide additional strength but which adds to the total weight and cost price of the speculum.

BRIEF SUMMARY OF THE DISCLOSURE

The inventor came to the realization that edges of the beaks can cause discomfort and injury to the patient in particular if the parting line which is associated with a moulding method is not properly positioned on the beak or blade edge, in particular its edge face.

The tissue lining the vaginal wall is only partially elastic and becomes less elastic over time. When inserting, rotating, opening and closing the speculum these edges come in direct contact with the lining of the vagina. During insertion of the speculum, muscle tissue of the vagina around the speculum is widened. The tissue lining the vaginal wall is thereby squeezed against the speculum. As the speculum is inserted the beaks are most commonly also rotated from a nearly vertical or 5 minutes past 7 orientation to a horizontal or quarter past 9 position as defined by the motion of fingers of a clock. There is generally a gap between the blades, thereby exposing at least part of the blade edges. Due to the rotating action of the speculum the blades, also called beak parts can become misaligned. This further increases the exposure of the thin blade edges. These thin edges scrape against the vaginal lining and in some instances can cause severe discomfort, distress and injury.

When a speculum is inserted the pivotable blades are subsequently at least partially distended or opened. Due to the constricting function of the vaginal muscle tissue around the speculum, lack of elasticity of the skin tissue lining the vagina wall and gravity tissue often tends to protrude basically into the space defined by the beak parts, thereby folding around the edges. The relatively thin edges can cause discomfort by allowing the tissue to make a sharp fold over these edges. This also causes localized pressure in the skin to build up over the narrow edges. This can limit blood flow and cause injury at prolonged exposure.

During a medical curative procedure the speculum blades can be placed over an internal structure or be used to move, lift, hold and or fixate an internal structure. In the case of the vaginal speculum the distal ends of the blades function as beaks placed over and or around the Cervix. The blades can also be used to lift or hold the Cervix. When the Cervix protrudes in between the distal ends of the blades or is held by their ends the thin edge at the end of one or more of the beak parts can also cause discomfort or injury as previously described for the side edges. Additionally, when the beak parts are used to move, lift, hold, grasp or otherwise manipulate the Cervix the edge comes in direct contact with the Cervix and can cause extra discomfort or injury due to the pressures being highly localized on the thin edges.

The injection moulded such as metal or plastic specula, due to the mould design, will usually have parting lines in the metal or plastic, where the mould halves meet. Where product surfaces meet at these parting lines, the angles between these surfaces are generally not rounded, but sharp edges. These parting lines can feel very sharp. What is described as in case of plastic a plastic flash, an unintentional very thin film or wall of plastic can form on these parting lines. These can have the unintentional function of a knife. Even when edges near parting lines are rounded an unintentional stepped parting line can also form at these locations when mould halves are not perfectly aligned. These can also feel extremely sharp since they generally have no radius, making sharp angles. These parting line edges are an additional source of common patient discomfort and injury.

Before closing the speculum the speculum may sometimes be retracted over a certain length. This causes extra aggravation, scraping and or injury to the tissue on the thin edges, especially on the parting lines of plastic specula.

When closing the speculum, tissue, which has protruded in-between the speculum beak parts can become pinched between the edges of the beak parts. The relatively thin edges cause uncomfortable to severe pinching of the tissue due to localized high pressure build-up. The thin edges also allow the tissue to practically fold back on itself, with only a thin beak in between. This makes closing difficult and painful for tissue to move out and away from the inside of the speculum beak parts. It causes additional discomfort, pinching, scraping and or injury.

During retraction of the speculum from the vaginal cavity, any discharge such as blood or other liquids or solids may easily spill over the edges, out of the beaks. This is not desirable for patient or doctor.

This invention seeks to provide a surgical instrument which is reusable, is lightweight, but nevertheless shows sufficient overall strength, without resulting in discomforts normally associated with in particular moulded speculum instruments.

In a first aspect of the present invention, a surgical instrument is provided having the features of claim 1.

In a further aspect of the present invention, a method for manufacturing the surgical instrument is provided.

DESCRIPTION OF THE DRAWINGS

In the following the invention is further explained by means of a number of non-restricting exemplary embodiments whereby.

DETAILED DESCRIPTION OF THE DISCLOSURE

Figure 1A:
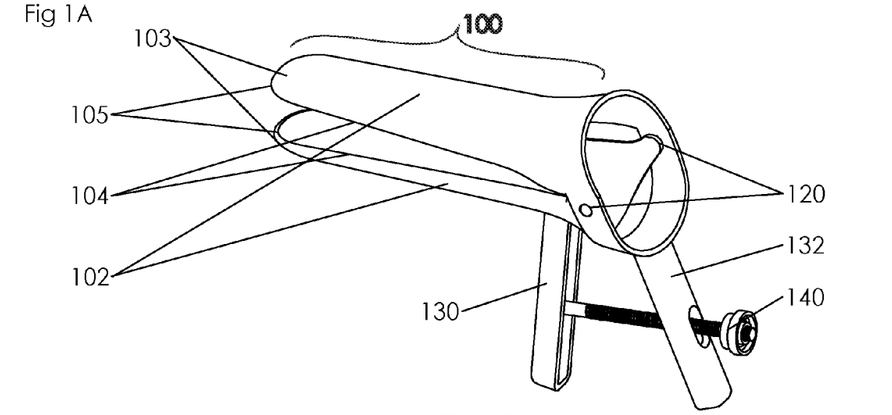
FIG. 1A shows a perspective view of an embodiment of a plastic speculum device according to prior art in the in a partially opened state.
Figures 1B, 1C, 1D:
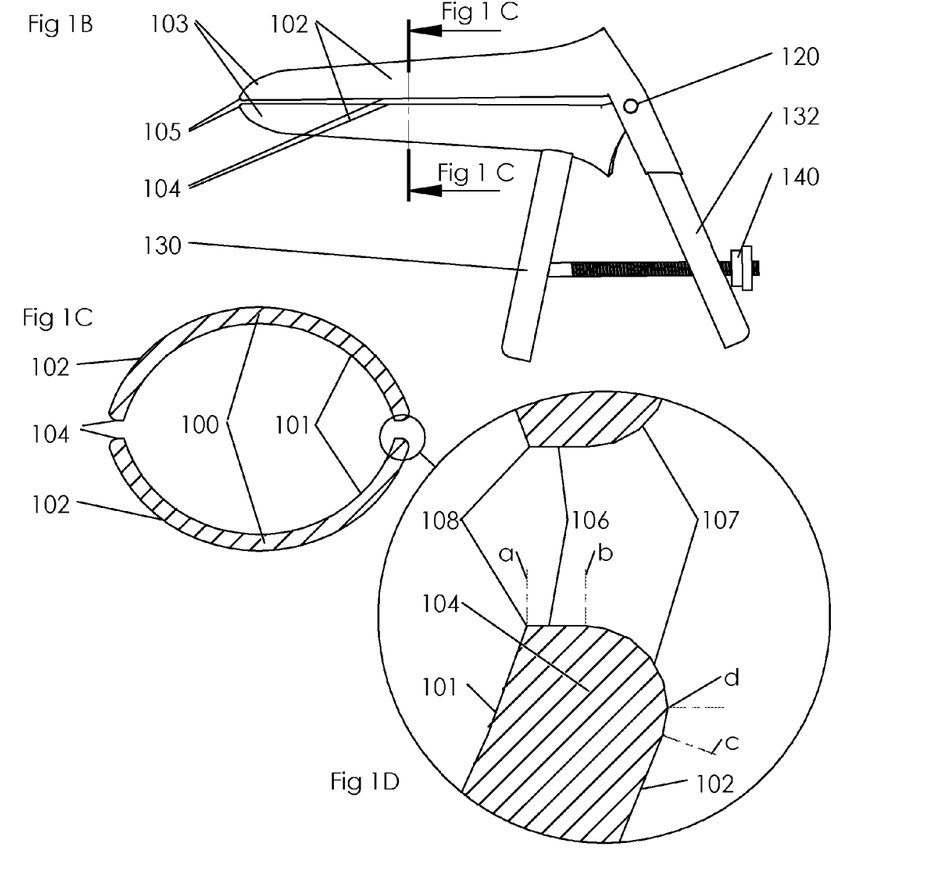
FIG. 1B shows a side view of the device according to FIG. 1A in a closed state.
FIG. 1C shows a cross-sectional view of the device according to FIG. 1B.
FIG. 1D shows a detailed view of the cross-sectional view FIG. 1C.

FIGS. 1A and 1B depict an embodiment of a commonly used Vaginal Speculum according to prior art, comprising blades or Beak Parts 100, with an Inner Surface 101 and an Outer Surface 102. The Beak Parts 100 have Beak Edges 104 and have Cupped Ends 103 at their respective distal ends. Cup Edges 105 form the edges of the Cupped Ends 103. The Beak Parts 100 are inserted into the vagina in a closed state with the Cupped Ends 103 initiating penetration. Hence the Cupped Ends are referred to as the distal end of the Beak Parts 100 in this application. The Beak Parts are typically coupled in such a way that they can move away from each other or towards each other in an angular or a lateral movement, or a combination of both, to expose part of the interior of the vaginal cavity.

Typically the common speculum has a Pivoting Joint 120 at the proximal ends of the Beak Parts 100. Once Beak Parts are inserted into the vaginal cavity the First Handle 130, and Second Handle 132 are moved towards each other, forcing the Beak Parts away from each other. Speculums according to prior art typically have a Locking Device 140 to allow fixing of the dilation of the cavity. (The design of the pivoting joint including the connection between the beak parts and the handle parts will not be discussed further here.)

During insertion of the Speculum into the vaginal cavity the speculum exerts pressure on the walls of the vagina, forcing the cavity to widen. The vaginal tissue, due to tissue tension, muscle tension and gravity, exerts an opposite force on the speculum. The vaginal lining is sensitive and easily traumatised during this process. The Outer Surface 102 of the Beak Parts 100 is typically smooth and has a relatively large radius. The outer Edges 104, 105 generally have a very limited radius or no radius and often exhibit a gap between the edges of opposing beak parts, allowing tissue to protrude partially in between the Edges 104, 105, even in the closed state. This protruding tissue is folded over and compressed against these sharper Edges 104, 105.

FIGS. 1C and 1D show a cross-sectional view of part of the Beak Parts 100 with Inner Surface 101, the Outer Surface 102 and the gap between the Beak Edges 104. During insertion the Speculum is typically rotated as it is being inserted, which causes additional scraping of the tissue lining the vagina. These edges with limited or no radii, therefore cause a localized increase of stretching, pressure, sharp folding and or friction on the vaginal lining, commonly causing particular discomfort, distress or injury.

FIG. 1D shows a detailed view of the Beak Edge 104 where the edge face or Edge End Surface 106, as defined between lines "a" and "b", forms the end of the Beak Edge 104 between Inner Surface 101 and Outer Surface 102. The Edge End Surface 106 and Outer Surface 102 commonly exhibit an Outer Radius 107, as defined between lines "b" and "c". FIG. 1D further depicts a sharp transition or edge 108. This is commonly the case for injection moulded Specula due to the mould Parting Line 108 between Edge End Surface 106 and Inner Surface 101.

It will be clear to those involved in moulding that Parting Lines between any cavity side mould block and core side mould block will inherently follow the outer circumference of an injection moulded product using linear motion metal injection tools, to ensure no negative draft angle when extracting hard plastic parts. When a slide or insert or such is used in the location where the parting line would normally form this inherently introduces a new closed loop parting line formed by the circumference of this additional mould part, encircling the location where the original parting line would have been formed, linking both ends of the interrupted outer circumference parting line. A parting line will inherently form on an injection-moulded part where two separate metal mould tool parts join. Inter alia, a parting line will be introduced around the inner circumference of any through hole in a plastic part where two mould halves meet, also called cut-off surface. Although parting lines can in some instances be removed or diminished after moulding, these processes are labour and cost intensive and typically considered unviable for low-cost disposable plastic parts.

Parting lines 108 appear as an edge as in FIG. 1D or when located on a surface intended to be smooth, as a rim. This rim can commonly be distinguished and often felt as a sharp edge. Parting lines can typically exhibit "flash", which is a very thin film of plastic, generally less than a few hundredths of a millimeter thick and occasionally extending up to a millimeter or more from the surface, which is formed between mould parts when they are not completely compatible. This incompatibility can inter alia be due to varying mould production tolerances or incorrect injection parameters and the likelihood commonly increases with mould usage. These parting lines and especially flash can cause discomfort and injury to patient. Therefore parting lines are not desired on any of the Beak Part surfaces that can come into direct contact with vaginal tissue.

The Parting Line 108 in the surgical instrument and the method for manufacturing it as presented here is desired as far inwards or away from the outer circumference "d" on Outer Radius 107 of the Beak Edges 104, 105 as depicted in FIGS. 1C and D as possible. Several plastic designs according to prior art exhibit a parting line around the outer circumference of the Beak Edges 104, 105, on the Outer Radius 107 at location "d" as depicted in FIG. 1D. This is directly and continuously in contact with the vagina and consequently considered an undesirable speculum design solution. The design solution as depicted in FIG. 1 exhibits a sharp angled transition between the Edge End Surface 106 and the Inner Surface 101. Protruding tissue will frequently protrude multiple millimeters into the space defined by the Beak Parts. Especially when closing the speculum, this will cause tissue to come in contact with and scrape over the Parting Line 108.

Figure 2:
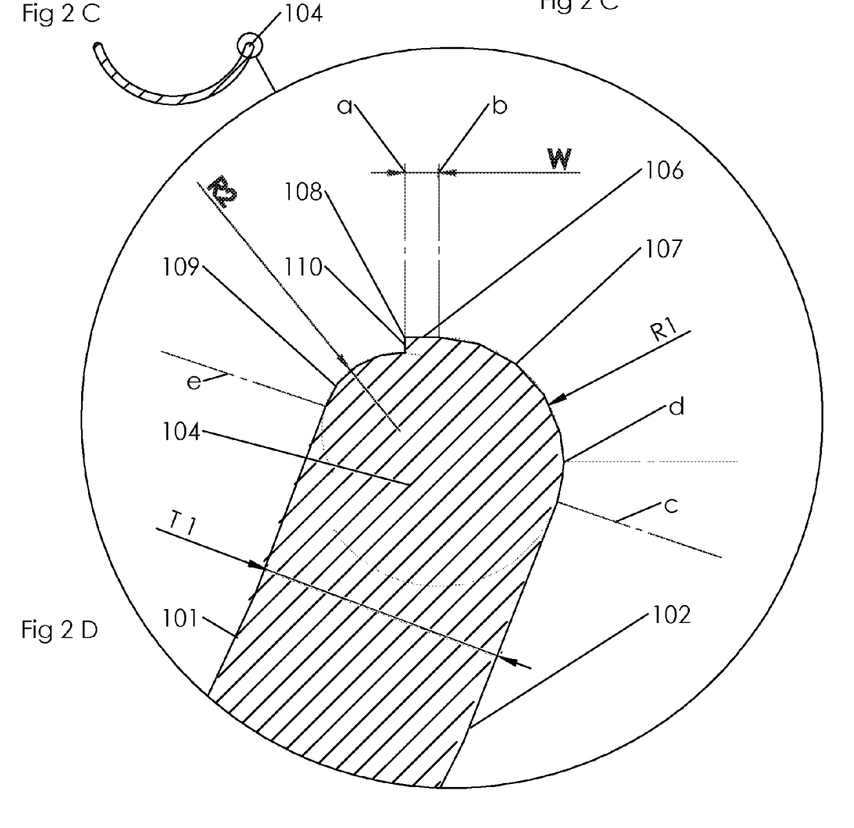
FIG. 2A shows a perspective view of a single Beak Part of an embodiment of a plastic injection moulded speculum according to a variation of FIG. 1 (A to D)
FIG. 2B shows a side view of the device according to FIG. 2A.
FIG. 2C shows a cross-sectional view of the thin edge of the side part of the beak according to FIG. 2B.
FIG. 2D shows a detailed view of the cross-sectional view FIG. 2C.

FIG. 2 depicts a variation on the location of the Parting Line 108 where an Inner Radius 109 between "a" and "e" has been added as a transition between Inner Surface 101 and Edge End Surface 106. FIG. 2D also depicts the Step 110, which will typically be noticeable on Parting Lines on continuous surfaces. This solution aims to reduce the effect of the sharply angled edge as depicted in FIG. 1. Introduction of a step can be intentional to guarantee the step is only noticeable from one direction. The parting line and occasional flash on the parting line is however moved closer towards the exterior of the Beak Parts, thereby increasing contact likelihood, frequency and duration with vaginal tissue.

The introduction and dimension "R2" of the Inner Radius 109 influences the width dimension "W" of the Edge End Surface 106 and or the radius dimension "R1" of the Outer Radius 107. The reduction of either the Edge End Surface or the Outer Radius further reduces the support given to protruding tissue and increases the sharpness of the folding of tissue. As the Speculum is closed, protruding tissue is pinched between opposing Beak Edges 104. Due to the reduced effective surface area of the Beak Edges 104, the localized pressure and resulting pinching sensation, discomfort and possible injury are amplified and thus undesirable. The Increase of the thickness "T1" of the blade or Beak Parts 100 would increase the effective surface area and move the parting line further inwards, however it will significantly increase material use and production costs, which are undesirable.

Metal specula commonly have rounded edges and no parting lines, however in steel Specula the rounded edge radius is commonly limited to 0.1 to 0.2 millimeter and due to the limited Beak Part thickness "T1" the effective surface area of the Beak Edges 104 reduces and sharp folding, pinching and scraping of the vaginal tissue increases, causing amplified irritation, trauma or injury.

Figure 3:
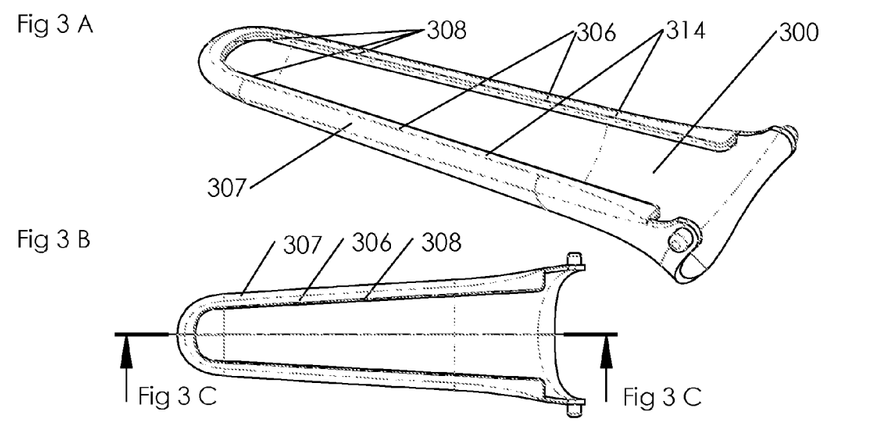
FIGS. 3A, 3B, 3C, 3D and 3E show respective views of a first embodiment of a surgical instrument according to the invention.

FIGS. 3A, B, C and D depict a first embodiment of a surgical instrument according to the invention embodying several advantages. An Inwardly Extended Edge (or Inwardly Curved Circumferential Edge) 314 is combined with the inside of blade or Beak Part 300, thereby creating a supporting device in the form of Inwardly Extended Supporting Surface 306. The edge 314 shields the thus inwardly repositioned parting line 308 preventing this from creating injuries. The increase of the Outer Radius 307 and the relocation of the parting line 308 also creates a strengthened rib-like structure, which may even have a virtually uniform thickness with a low own weight.

The supporting surface 306 device is intended for manipulating, supporting, holding or clasping tissues such as the Cervix by using the Inwardly Extended Surface 306 of the Inwardly Extended Edge 314 near the Cup Edge 305 of the Cupped End 303. The Cup Edge is part of the Beak Edge 304 and is specifically located at the Cupped End 303. The manipulated tissue surface, inter alia, the Cervix, is sensitive and the substantially flat and enlarged surface Inwardly Extended Surface 306 enables the distribution of the load or pressure exerted on the Cervix. Tissue that unintentionally protrudes in between the Beak Edges 304 is supported by the substantially flat Inwardly Extended Surface 306. Furthermore the Inwardly Extended Edges 314 allow for the deliberate manipulation of these side tissues whilst significantly reducing discomfort, trauma and injury. The Inwardly Extended Edge 314 can also be used to help support, stabilize or let rest any tools or instruments which may be used during procedures in combination with specula, such as bipolar coagulation devices.

This embodiment further introduces a shielding function created by means of the enlarged Outer Radius 307, which through this invention is able to have a radius "R1", which can be of a dimension larger than the thickness dimension "T1" of the Beak Part 300 and which does not require any increase of thickness at or near the Beak Edge 304 or Inwardly Extended Edge 314, as depicted in FIG. 3D. The thickness dimension "T3" and "T2" of Beak Edge 304 and Inwardly Extended Edge 314 respectively can effectively be of a thickness smaller than the thickness "T1" of the Beak Part. The increase of the radius dimension for the Outer Radius 307 effectively reduces inter alia the scraping, pinching, sharp folding, and limiting of blood flow.

The introduction of the Inwardly Extended Edge 314 further allows the Parting Line 308 to be moved further away from the Beak Edge 304 and any protruding tissue without the need to increase the Beak Part 300 thickness dimension "T1", which is located between the Inner Surface 301 and Outer Surface 302. This will be explained in more detail below.

The combinations of advantageous features described here significantly reduce scraping and pinching of the vaginal tissue, significantly reduce the point load or local increase of pressure by distributing the load more evenly, significantly reduce the risk of tissue coming into contact with the parting line, the force with which it can be forced onto or over the parting line and significantly reduce the sharpness of the tissue folding around the edges, thereby significantly decreasing levels of patient discomfort, trauma and injury, effectively shielding the vaginal tissue from sharp edges. This combination of one or more of these inventions (combination of devices) is especially desirable or critical when the patient experiences vaginal symptoms of irritation, infection or soreness, but is not limited to these conditions and may be substituted by any other condition.

Tissue which does protrude beyond the Inwardly Extended Edge 314 will merely be influenced by gravity. Therefor during the vast majority of common Gynaecological handlings, which require a speculum, tissue will not be pressed against Inwardly Extended Edge End Surface 313 or Surface 312, thereby further shielding the tissue from discomfort, damage or injury. The comparatively thin Edge End Surface 106 as depicted in prior art examples FIGS. 1 and 2 has hereby effectively been shielded.

The Inwardly Extended Edge 314 is able to retain fluids and discharge as the speculum is retracted from the Vagina. This is both more comfortable and less confronting for the patient and very practical for the Physician. It may also reduce or negate the need for a suction device, reducing the quantity of medical instruments and the complexity of handlings required.

The introduction of the Inwardly Extended Edge introduces a strengthened surgical instrument by effectively forming a version of a rib on the inside of the Beak Part on the Inner Surface 301, thereby having a strengthening and stiffening effect on the Beak Part 300. This could allow for the "T1" thickness dimension of the Beak Part 300 to be reduces whilst maintaining sufficient strength and stiffness for the speculum to fulfil it's function adequately. Reduction of thickness and thus weight can have cost saving effect on injection moulding cycle time and material used.

In FIG. 3D the Inwardly Extended Surface 306 is depicted as a predominantly flat surface between the curved surfaces 309 and 307 and with parting line at one end at location "a". It is preferred that the Inwardly Extended Surface 306 is oriented such that it is principally at least partially parallel to an opposing or adjacent Beak Part with possibly a similar Inwardly Extended Surface when in closed position or state. When the surfaces are predominantly parallel, the distribution of load or pressure on protruding tissue, when Beak Parts are closing, is best and most evenly distributed and inter alia as such preferable. The location of the Parting Line 308 is not restricted to the location between Inwardly Extended Surface 306 and the Inner Radius Surface 309. In a standard injection mould configuration the Parting Line 308 is located at the outer circumference of a part. Depending on the shape, orientation and design of the Inwardly Extended Edges 314 of the Beak Parts 300 of a speculum, the quantity of Beak Parts and the design of a speculum, the location of the Parting line or lines can vary. When the Inwardly Extended Edge is oriented or angled slightly outwards and away from or angled more towards the Inner Surface 301 the Parting Line 308 may inter alia be located on or at surfaces 309 or 307 respectively. A Parting line 308 on the Inner Radius surface 309 would inter alia be practical in Speculum embodiments with more than 2 Beak Parts, in order to allow adjacent Inwardly Extended Edge Surfaces of adjacent Beak Parts to be predominantly parallel. It should be understood that the location of the Parting Line of Beak Parts is desired such that it is optimal for the patient. The choice of a different location of the parting line such as on surfaces 307 or 309 does not negate the novel combination of features and resulting novel manufacturing and or functional advantages in this application for specula. A visible parting line may not be a requirement for this application, inter alia, when using steel to make the Speculum.

Figure 4:
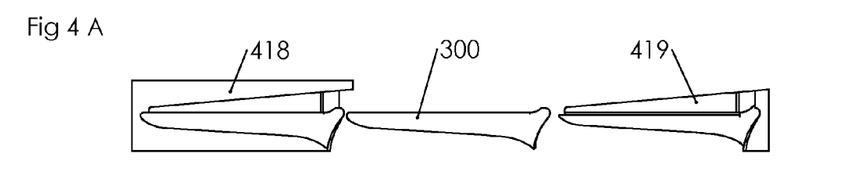
FIGS. 4A, 4B, 4C, 4D, 4E and 4F show various respective steps of the method of manufacturing the surgical instrument of FIG. 3.
Figure 5:
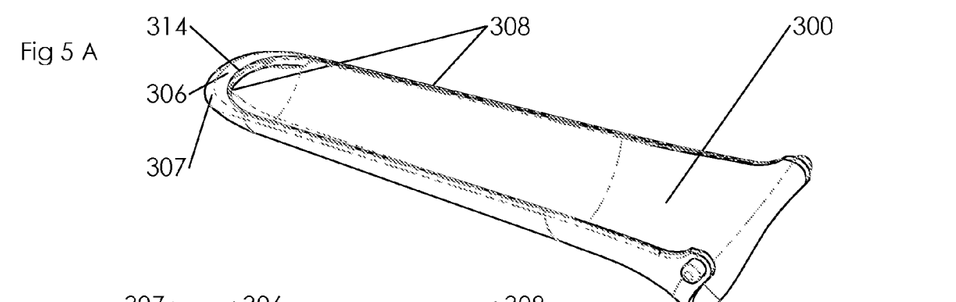
FIGS. 5A, 5B, 5C, and 5D show respective views of a second embodiment of a surgical instrument according to the invention.

FIG. 4 depicts an embodiment of part of a basic injection mould tool build-up, including only a Cavity Block 418 and a Core Block 419, which is needed to achieve the manufacture of a plastic injection moulded Beak Part comprising the combination of features in this application when this combination is made in one single injection-moulding step as one single part. (All other mould parts, which comprise an injection-moulding tool, are ignored in this description.) During each injection cycle the Cavity and Core Blocks are pressed together with a linear Clamping Force, which is in line with the linear motion, to overcompensate the pressure the injected plastic exerts on the mould. When the Blocks are in closed position, the Cavity Block and Core Block meet at the Parting Surface 408, forming a seam at the edges of the mould blocks. This seam causes the Parting Line 308 to form on the part as the plastic hardens. Consequently the design and construction requirements of the mould define parameters for the location of the Parting Line 308. The Mould Block Parting Surface 408 requires a draft angle, which is angular to the linear motion and Clamping Force, initially to allow the Core Block to slide into the Cavity Block and sequentially to allow the opposing mould blocks to exert clamping force on one another at the Parting Surface 408, preventing plastic from flowing into the seam and forming flash, etc. The angle "A°" at which the blocks are pressed together influences the wear on the connecting surfaces at the Parting Surface and thus the mould accuracy and lifespan. Typically an angle "A°" of at least one degree is needed and larger is significantly preferred.

Generally injection moulded parts require all surfaces to have a zero or positive draft, as is the case for the Beak Parts, inter alia, surfaces 301, 302, 306, 307, 309 and 312. (Slides do not offer a solution for further removing parting lines from the Beak Parts and as such are ignored.) The Parting line 308 in this embodiment is flanked by Inward Extended Surface 306 and Inner Radius Surface 309 whereby the former is formed by the Cavity Block 418 and the latter by the Core Block 419. Hence only a zero or close to zero degree draft angle at both parts of the surfaces flanking the parting line will allow both to correctly de-mould without the introduction of an obvious step or ridge. Effectively the Parting Line 308 on the Beak Edges 304, 314 is required to be in a flat plane parallel to the linear motion (open-close motion) of the injection mould. If the Inner Radius 309 were abandoned in this embodiment the functional design intent according to the combination of devices in this application would still be effective. Without the Inner Radius 309 a minor draft angle could in limited instances be introduced, however this is only applicable in embodiments where the width of the Beak Part (W4 to W3) and or the radius of the Outer Edge 307 tapers towards the distal end thereof and the Parting Line 308 would form a sharp edge.

In FIG. 4F the width "W 3" at the distal end of the Beak Part 300, near the Cupped End 303 thereof, is limited by the width "W 4" of the Beak Part near the proximal end thereof. The Beak Part surfaces 301, 302, 306, 307, 309 and 312 require a draft angle of zero degrees or larger for the part to de-mould (come out of the mould) properly. Thus the width "W 3" near the distal end can be equal to or smaller than the width "W 4". A larger width would result in negative draft and damage the part during opening of the mould or not allow opening of the mould. In Prior art the width "W 3" and angle "a°" of Plastic Injection Moulded Specula is typically limited by the angle "A°" required by the parting line. The Inwardly Extended Edge 314 in this combination of devices effectively allows for the separation of dependency between the Parting Line 308 angle "A°" and the draft angle of the Outer Radius 307 by varying the width "W 1" and "W 2" of the Inwardly Extended Edge 314.

Now several non-limiting variations of embodiments of the combination of some or all of the features as previously described will be explained.

FIG. 4F depicts an embodiment of the combination of features where the width of the supporting surface is not constant.

FIGS. 5A, 5B, 5C, and 5D depict an embodiment of the combination of features in the surgical instrument, whereby the Distal end of the Beak Part 300 is combined with the supporting feature in the form of the Inwardly Extended Surface 306 of the Inwardly Extended Edge 314 at the Cupped End 303 thereof. The shielding is implemented by enabling the creation of the Outer Radius 307, of which the radius dimension can be larger than the thickness of the Beak Part, without the need to locally increase the part thickness and by enabling the distancing of the Parting Line 308 from the Beak Edge 304.

Figure 6:
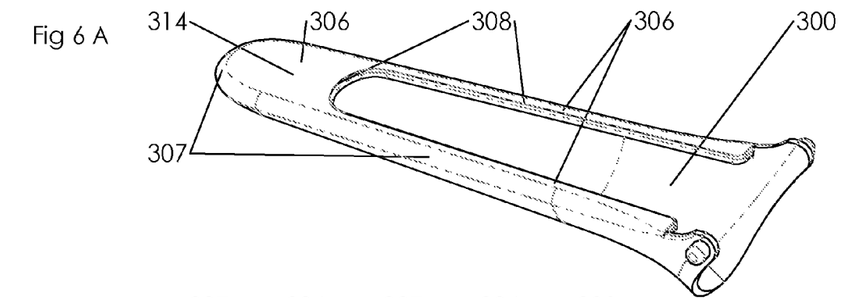
FIGS. 6A, 6B, and 6C show respective views of a third embodiment of a surgical instrument according to the invention.

FIGS. 6A, 6B and 6C depict an embodiment of the combination of devices where the width of the supporting device at the Cupped End 303 of the Beak Part 300 is increased. This enlarged supporting device is combined with supporting devices on Beak Edges 304 on Both sides of the Beak Part 300. This combination provides more support surface for tissue and utensils. It also enables the further shielding of the patient by further distancing the Parting Line 308 from the patient.

Figure 7:
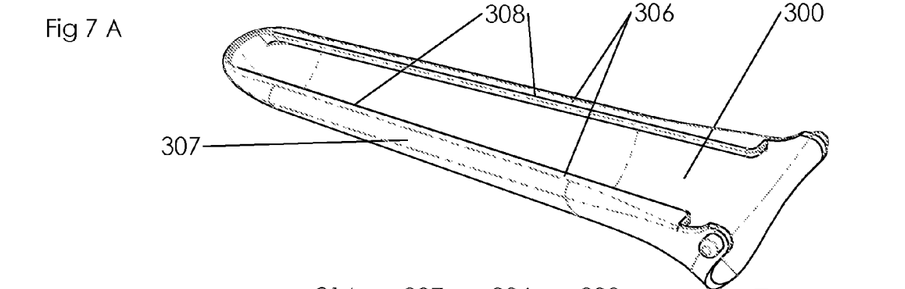
FIGS. 7A and 7B show views of a fourth embodiment of the surgical instrument according to the invention.

FIGS. 7A and 7B depict an embodiment of the combination of features in the surgical instrument where only parts of the Beak Edge 304 have been combined with the Outwardly Extended Edges 314. This combination provides more shielding and support surface on parts of the sides of the Beak Parts 300.

Figure 8:
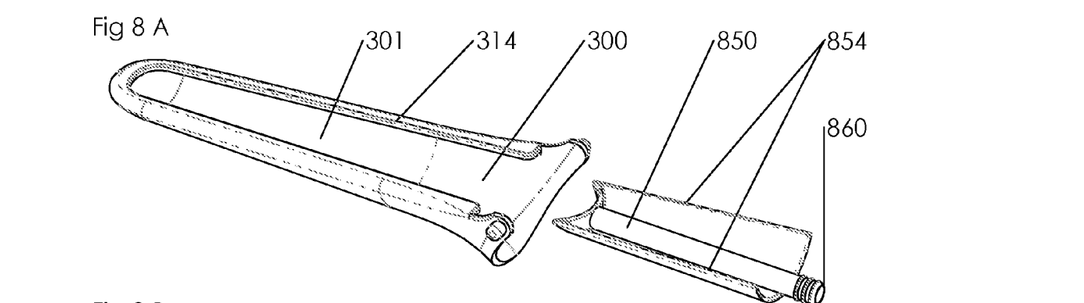
FIGS. 8A and 8B show views of a fifth embodiment of the surgical instrument according to the invention.

FIGS. 8A and 8B depict an embodiment of the combination of features where an insert device 850 is depicted, able to make a sliding connection with the Beak Part 300. The Outwardly Extended Edges 314, in collaboration with the Inner Surface 301 enable the holding in place of an insert 850. The insert here depicted resembles an insert for suction of inter alia fluids and smoke, by attaching a suction hose to a Nozzle 860. Part of the insert is oriented such that it, in this embodiment the edges 854, can make a connection with the Outwardly Extended Edges 314. An insert could amongst others encompass a device for suction, positioning and holding of surgical instruments, a light etcetera.

Figure 9:
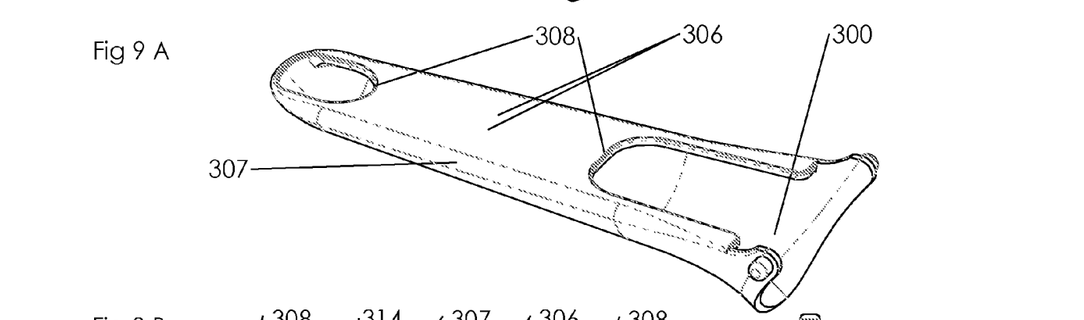
FIGS. 9A, 9B and 9C show views of a sixth embodiment of the surgical instrument according to the invention.

FIGS. 9A, 9B and 9C depict an embodiment of the combination of features in the surgical instrument where the Inwardly Extended Edges 314 of part of each side of the Beak Part 300 at least partially join. This effectively reduces and partially allows the moving away of the Parting Lines 308 towards the Proximal end or the Beak Part. A second closed parting line 308 is introduced near the Distal End or Cupped End 303 of the Beak Part. This second parting line can be moved away from the edges as described in this application. This second parting line could be formed by an Injection Mould Slide part. These at least partially joined Inwardly Extended Edges 314 provide extra structural strength and support to protruding tissue.

Figure 10:
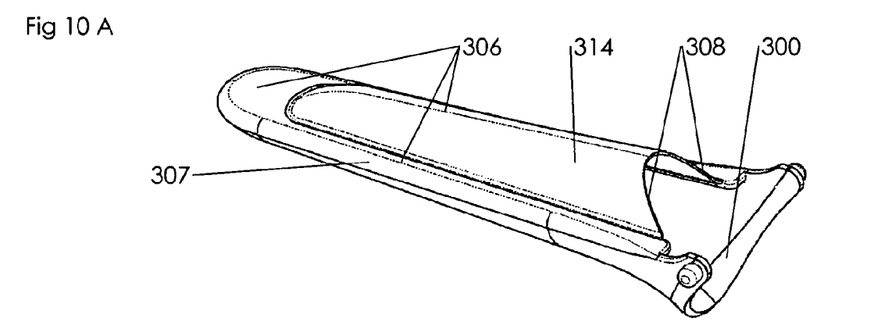
FIGS. 10A, 10B, 10C and 10D show views of a seventh embodiment of the surgical instrument according to the invention.

FIGS. 10A, 10B, 10C and 10D depict an embodiment of the combination of features in the surgical instrument where the Inwardly Extended Edges 314 of part of each side of the Beak Part 300 at least partially join. In this embodiment the Parting line 308 is limited to a small area near the Proximal end of the Beak Part. The Inwardly Extended Edges 314 Join in the middle and have an extra outwardly oriented dome shape as depicted in FIGS. 10A and 10B. This Dome shape is dimensioned as more thin than the surrounding Beak Part thickness and can therefore be pressed or flipped inwards by pressing down on the dome. The Dome part of the Inwardly Extended Edges 314 will then take a new position as depicted in FIGS. 10C and 10D, and remain in this new position due to the internal stresses of the material. This inwardly pressed Dome reduces the obstruction of the space and visual field inside the cavity defined by the Beak Part or parts.

The combination of features as described and depicted is not limited to these embodiments, all combinations, practices, production methodology, functions and advantages described can be combined and transferred. The exemplary lower Beak Part as depicted from FIG. 3 onwards is not limiting. It may apply to any of the Beak Parts of a Speculum. A Speculum is not limited to a maximum number of beak parts. For example three or more beak parts in a Speculum are also common.

The invention claimed is:

1. An instrument comprising elongated cup-shaped pivotably mounted blades manufactured from a mouldable material, wherein at least one blade has an inwardly curved circumferential edge provided with a parting line resulting from moulding the blade, which circumferential edge has a supporting surface including an outer radius surface, an inwardly extended surface, and an inner radius surface, wherein the parting line is provided on one of, or between, the outer radius surface and the inner radius surface of the supporting surface, and away from the blade outer circumference.

2. The instrument according to claim 1, wherein the supporting surface faces a supporting surface of an inwardly curved circumferential edge of an opposite or adjacent blade.

3. The instrument according to claim 1, wherein the inner radius surface and the outer radius surface, respectively are inwardly curved.

4. The instrument according to claim 1, wherein the parting line lies at or near the inner radius surface of the supporting surface.

5. The instrument according to claim 2, wherein each blade is pivotably mounted on one short side and the supporting surface extends at the opposite short side of the blade.

6. The instrument according to claim 1, wherein the blade has an inwardly curved circumferential edge almost completely surrounding the blade.

7. The instrument according to claim 1, wherein the material of the blade has a virtually uniform thickness seen over its section.

8. The instrument according to claim 1, wherein the inwardly curved circumferential edge defines a lower insertion cavity for holding an insert.

9. The instrument according to claim 1, wherein the instrument comprises a manually operable locking device coupling two blades allowing opening and fixation of the blades in different angular positions.

10. A method of manufacturing an elongated cup-shaped blade for a surgical instrument, comprising positioning mould halves in a blade moulding process resulting in a parting line induced on the blade, wherein the blade has an inwardly curved circumferential edge having a supporting surface including an outer radius surface, an inwardly extended surface, and an inner radius surface, wherein, in the blade moulding process, the parting line is provided on one of, or between, the outer radius surface and the inner radius surface of the supporting surface, away from the blade outer circumference.

11. The method according to claim 10, wherein the parting line lies closest to, or at, the inner radius surface of the supporting surface.

12. The instrument according to claim 1, wherein the mouldable material is plastic or metal.

13. The instrument according to claim 1, wherein a radius of the outer radius surface is of a dimension larger than a thickness dimension of the blade.

14. The instrument according to claim 1, wherein a thickness dimension of the circumferential edge is of a thickness smaller than a thickness of the blade.

15. The instrument according to claim 1, wherein a thickness dimension of a beak edge is of a thickness smaller than a thickness of the blade.

16. The instrument according to claim 1, wherein a width near a distal end of the blade is equal to or smaller than a width near a proximal end of the blade.

17. The instrument according to claim 1, wherein the instrument is a surgical instrument.

18. The instrument according to claim 17, wherein the instrument is a speculum.

* * * * *